United States Patent
Belguith et al.

(10) Patent No.: US 6,372,476 B1
(45) Date of Patent: Apr. 16, 2002

(54) POLYPEPTIDES HAVING GLUCOSE ISOMERASE ACTIVITY AND NUCLEIC ACIDS ENCODING SAME

(75) Inventors: Karima Srih Belguith; Radhouane Ellouz; Samir Bejar, all of Sfax (TN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/383,318

(22) Filed: Aug. 26, 1999

(30) Foreign Application Priority Data

May 26, 1999 (TN) ................................................ 99.100

(51) Int. Cl.⁷ .............................. C12N 9/90; C12N 1/21; C12N 15/52; C07H 21/04
(52) U.S. Cl. ............... 435/233; 435/252.3; 435/252.35; 435/320.1; 536/23.2
(58) Field of Search ......................... 435/252.3, 252.35, 435/320.1, 233; 536/23.2

(56) References Cited

PUBLICATIONS

Belghith–Srih (Feb. 1, 1999) Genbank accession Y15518.*
Bejar et al., Biotechnology Letters, vol. 16, No. 12, pp. 1259–1264 (Dec. 1994).
Meaden et al., Gene, vol. 141, pp. 97–101, (1994).
Wuxiang et al., Biotechnology Letters, vol. 15, No. 11, pp. 1101–1106 (Nov. 1993).
Brown et al., Biotechnology and Bioengineering, vol. 41, pp. 878–886 (1993).
Dekker et al., Appl. Microbiol. Biotechnol., vol. 36, pp. 727–732 (1992).
Belghith et al., Biotechnology Letters, vol. 20, No. 6, pp. 553–556 (Jun. 1998).
Wong et al., Journal of Bacteriology, vol. 173, No. 21, pp. 6849–6858 (Nov. 1991).

* cited by examiner

*Primary Examiner*—Elizabeth Slobodyansky
(74) *Attorney, Agent, or Firm*—Elias Lambils; Jason Gavbell

(57) ABSTRACT

Disclosed are isolated polypeptides having glucose isomerase activity selected from:

(a) a polypeptide having an amino acid sequence which has at least 95% identity with amino acids of SEQ ID NO:2;

(b) a variant of the polypeptide having an amino acid sequence of SEQ ID NO:2 comprising a substitution, deletion, and/or insertion of one or more amino acids;

(c) a fragment of (a) that has glucose isomerase activity; and (d) a polypeptide having a pH optimum in the range of 5.7 to 6.3 at 60° C., a pH optimum in the range of 6.1 to 6.7 at 90° C and a temperature optimum of above 90° C. Also disclosed are isolated nucleic acid sequences encoding the polypeptides, nucleic acid constructs, vectors, and host cells comprising the nucleic acid sequences as well as methods for producing and using the polypeptides.

5 Claims, 5 Drawing Sheets

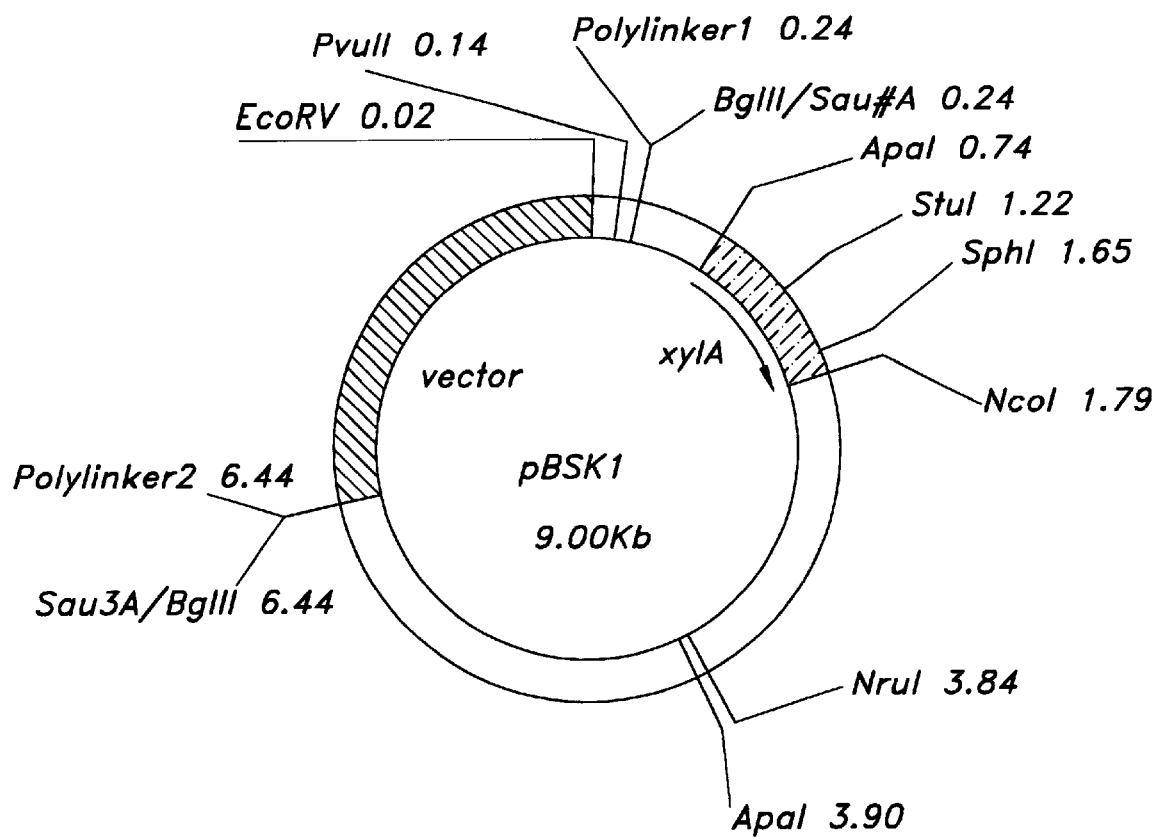
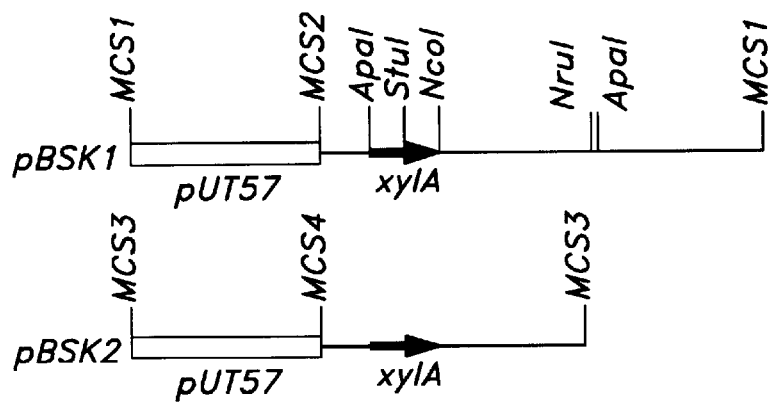
FIG 3

```
CACGAGCGCCCTTGGTGTGGACTGGGTCCACACCGACGACGAGGGCGACCCTCGGCTGCTGACATCGGCTCTCCCTCTTTTTCCCGGCTCAGGGG         100
CTCTGACCTGCGGCTTCACGCTATGCCGGGCCTGTGGGCCCCGGGGTGCCGGGACCCGTTTCTGCTTCCGGTTCCCTTCCCAGGGACGGGG                200
TCGGCATACTAATTTGTAAATCGCCCTGACGAAATAGTGCAAGCGAGCAAGGAGCCGGCATGAACTACCAGCCCACCCCGAGGACAGGTTCACCTT           300
                                                            M  N  Y  Q  P  T  P  E  D  R  F  T  F         13
CGGCCTGTGGACCGTCGGCCTCCAGGGGCGGGACCCCTTCGGCGACGCCACGCGTCCCGCCCTCGACCCGGTGGACGTGCAGCGGCTGGCCGAACTGGGC      400
 G  L  W  T  V  G  W  Q  G  R  D  P  F  G  D  A  T  R  P  A  L  D  P  V  D  V  Q  R  L  A  E  L  G        46
GCCTACGGAGTGACCTTCCACGACGACCTGATCCCCTTCGGGGCGTCCGACACGGAGCGCGAGGCGCACGTCAAGCGGTTCCGTCAGGCGCTCGACG         500
 A  Y  G  V  T  F  H  D  D  L  I  P  F  G  A  S  D  T  E  R  E  A  H  V  K  R  F  R  Q  A  L  D          79
CGACCGGCATGACCGTTCCGATGGCCACCACCAACCTCTTCACCCACCCCGTCTTCAAGGCAGGCGCGTTCACCGCCAACGACCGCGCAGTGCGCCGTTA      600
 A  T  G  M  T  V  P  M  A  T  T  N  L  F  T  H  P  V  F  K  A  G  A  F  T  A  N  D  R  A  V  R  R  Y    113
CGCCCTGCGCAAGACCATCCGGAACATCGATCTCGCGGTCGAGCTCTACGTCGCCAAGGTCTACGTGGGCGCCTTGAGCTCCGTCGCCAAGTCCGGTGCC      700
 A  L  R  K  T  I  R  N  I  D  L  A  V  E  L  G  A  K  V  Y  V  V  A  W  G  G  R  E  G  A  E  S  G  A    146
GCCAAGGACGTGCGCGCCCTGGACCGGATGAAGGAGGCCTTCGACCTGCTCGGCGAGTACGTCACCTCGCAGGGCTACGACATCCGGTTCGCCATCG         800
 A  K  D  V  R  A  A  L  D  R  M  K  E  A  F  D  L  L  G  E  Y  V  T  S  Q  G  Y  D  I  R  F  A  I       179
```

FIG 4A

```
AGCCCAAGCCCGAACGAGCCGCGGGGACATCCTGCTGCCCACCATCGGCCACGCGCTCGCCTTCATCGAGCGCCTGGAGCGCCCCGAGCTGTCCGGTGT    900
 E  P  K  P  N  E  P  R  G  D  I  L  L  P  T  I  G  H  A  L  A  F  I  E  R  L  E  R  P  E  L  Y  G  V   213

CAACCCCGAGGTGGGCCACGAGCAGATGGCCGGCCTGAACTTCCCGCACGGCATCGCGCAGGCTCTGTGGGGGCAAGCTCTTCCACATCGACCTCAAC   1000
 N  P  E  V  G  H  E  Q  M  A  G  L  N  F  P  H  G  I  A  Q  A  L  W  A  G  K  L  F  H  I  D  L  N    246

GGCCAGTCCGGCCATCAAGTACGACCAGGACCTGCGCTTCGGCGCCGGTGACCTGCGCGCCCTTCGGCTGTCGACTGGAGAGCGCCGGCTGGG        1100
 G  Q  S  G  I  K  Y  D  Q  D  L  R  F  G  A  G  D  L  R  A  A  F  W  L  V  D  L  L  E  S  A  G  W   289

AGGGTCCGCCACTTCGACTTCAAGCCCCCGCGGACCGAGGACATCGACGGCGTGTGGGCCTCCGCGGCCGGGTGCATGCGCAACTACCTGATCCTGAA   1200
 E  G  P  R  M  F  D  F  K  P  P  R  T  E  D  I  D  G  V  W  A  S  A  A  G  C  M  R  N  Y  L  I  L  K  313

GGAGCGCGCCGCCGCCTTCCGTGCCGACCCGGAGTTCAGGCCGAGGTCCAGGAGGTCCAGGAGGTCCAGGAGGCCCGAGCCCACCGGCGACGGCCTG   1300
 E  R  A  A  A  F  R  A  D  P  E  V  Q  E  A  L  R  A  A  R  L  D  Q  L  A  E  P  T  A  A  D  G  L    346

CAGGCCCTGCTGGCCGACCGCACCGCGTACGAGGACTTCGACGTGGACGCGGCGGCCCGCGGCATGGCCTTCGAGCGCCTCGACCAGCTCGCCATGGACC   1400
 Q  A  L  L  A  D  R  T  A  Y  E  D  F  D  V  D  A  A  A  R  G  M  A  F  E  R  L  D  Q  L  A  M  D    379

ACCTGCTGGGCGCCCGCGGCTGAACCGGGCGACGAGGGGTACGCGGTCGATCTCCCTGCGTCGTCATGAGGGGTGCTGGGCGGCTCGAGGCGGCCC   1500
 H  L  L  G  A  R  G  ***                                                                          386

GGCCCCATCGTGCTGCGTCTCCCCGGGGCGCCGGTGTGGGCCGTGTGC                                                   1546
```

*FIG 4B*

```
XYLA-STRSK   99-A₁₀₀-G-A₁₀₂-FTANDR-A₁₀₉-VRR-113
XYLA-STROL   99-D₁₀₀-G-G₁₀₂-FTANDR-D₁₀₉-VRR-113
XYLA-STRVO   99-D₁₀₀-G-G₁₀₂-FTANDR-D₁₀₉-VRR-113
XYLA-ACTMI   99-D₁₀₀-G-G₁₀₂-FTSNDR-S₁₀₉-VRR-113
XYLA-AMPSP   99-D₁₀₀-G-G₁₀₂-FTSNDR-S₁₀₉-VRR-113
XYLA-THETH   99-D₁₀₀-G-A₁₀₂-FTSNDR-W₁₀₉-VRR-113
```

FIG 5

SEQUENCE LISTING

```
<160> NUMBER OF SEQ ID NOS: 7

<210> SEQ ID NO 1
<211> LENGTH: 1546
<212> TYPE: DNA
<213> ORGANISM: Streptomyces

<400> SEQUENCE: 1
cacgagcgcc ttggtggact gggtggacga gtccacaccg acgacgaggc ggaccctcgg      60
ctgctgacat cggctctccc tcttttttccc ggctcagggg ctctgacctg cggcttcacg     120
ctatgccggg cctgtgggcc ccggggtgcg gacccggccc ggcccgtttc tgcttccgcg     180
ttcccttccc agggacgcgc tcggcatact aatttgtaaa tcgccctgac gaaatagtcg     240
caagcgagca aggagccgcg gcatgaacta ccagcccacc cccgaggaca ggttcacctt     300
cggcctgtgg accgtcggct ggcaggggcg ggaccccttc ggcgacgcca cgcgtcccgc     360
cctcgacccg gtcgacgtgc agcggctggc cgaactgggc gcctacggag tgaccttcca     420
cgacgacgac ctgatcccct tcggggcgtc cgacaccgag cgcgaggcgc acgtcaagcg     480
gttccgtcag gcgctcgacg cgaccggcat gaccgttccg atggccacca ccaacctctt     540
cacccacccc gtcttcaagg caggcgcgtt caccgccaac gaccgcgcag tgcgccgtta     600
cgccctgcgc aagaccatcc ggaacatcga tctcgcggtc gagctgggcg ccaaggtcta     660
cgtcgcctgg ggcggccgcg agggcgcgga gtccggtgcc gccaaggacg tgcgtgcggc     720
cctggaccgc atgaaggagg ccttcgacct gctcggcgag tacgtcacct cgcagggcta     780
cgacatccgg ttcgccatcg agcccaagcc gaacgagccg cgcggcgaca tcctgctgcc     840
```

-continued

```
caccatcggc cacgcgctcg ccttcatcga gcgcctggag cgccccgagc tgtacggtgt    900 caacccccgag gtgggccacg agcagatggc cggcctgaac ttcccgcacg gcatcgcgca    960
ggctctgtgg gcgggcaagc tcttccacat cgacctcaac ggccagtccg gcatcaagta   1020
cgaccaggac ctgcgcttcg cgccggtga cctgcgcgcc gccttctggc tggtcgacct   1080
gctggagagc gccggctggg aggtccgcg ccacttcgac ttcaagcccc gcggaccga   1140 ggacatcgac ggcgtgtggg cctccgcggc cgggtgcatg cgcaactacc tgatcctgaa   1200
ggagcgcgcc gccgccttcc gtgccgaccc ggaggtccga gaggccctgc gtgccgcccg   1260
gctcgaccag ctcgccgagc ccaccgcggc cgacggcctg caggccctgc tggccgaccg   1320
caccgcgtac gaggacttcg acgtggacgc ggccgcgcgc ggcatggcct tcgagcgcct   1380
cgaccagctc gccatggacc acctgctggg cgcccgcggc tgaaccgggc gacgaggggg   1440
tacgcgcggt cgatctccct gcgtcgtcat gaggggtgc tgggcggctc gaggcggccc   1500
ggccccatcg tgctgcgtct cccggggcgc ggtgtggggc gcgtgc              1546
```

<210> SEQ ID NO 2
<211> LENGTH: 386
<212> TYPE: PRT
<213> ORGANISM: Streptomyces

<400> SEQUENCE: 2

```
Met Asn Tyr Gln Pro Thr Pro Glu Asp Arg Phe Thr Phe Gly Leu Trp
  1               5                  10                  15

Thr Val Gly Trp Gln Gly Arg Asp Pro Phe Gly Asp Ala Thr Arg Pro
             20                  25                  30

Ala Leu Asp Pro Val Asp Val Gln Arg Leu Ala Glu Leu Gly Ala Tyr
         35                  40                  45

Gly Val Thr Phe His Asp Asp Leu Ile Pro Phe Gly Ala Ser Asp
     50                  55                  60

Thr Glu Arg Glu Ala His Val Lys Arg Phe Arg Gln Ala Leu Asp Ala
 65                  70                  75                  80

Thr Gly Met Thr Val Pro Met Ala Thr Thr Asn Leu Phe Thr His Pro
                 85                  90                  95

Val Phe Lys Ala Gly Ala Phe Thr Ala Asn Asp Arg Ala Val Arg Arg
            100                 105                 110

Tyr Ala Leu Arg Lys Thr Ile Arg Asn Ile Asp Leu Ala Val Glu Leu
        115                 120                 125

Gly Ala Lys Val Tyr Val Ala Trp Gly Gly Arg Glu Gly Ala Glu Ser
    130                 135                 140

Gly Ala Ala Lys Asp Val Arg Ala Ala Leu Asp Arg Met Lys Glu Ala
145                 150                 155                 160

Phe Asp Leu Leu Gly Glu Tyr Val Thr Ser Gln Gly Tyr Asp Ile Arg
                165                 170                 175

Phe Ala Ile Glu Pro Lys Pro Asn Glu Pro Arg Gly Asp Ile Leu Leu
            180                 185                 190

Pro Thr Ile Gly His Ala Leu Ala Phe Ile Glu Arg Leu Glu Arg Pro
        195                 200                 205

Glu Leu Tyr Gly Val Asn Pro Glu Val Gly His Glu Gln Met Ala Gly
    210                 215                 220

Leu Asn Phe Pro His Gly Ile Ala Gln Ala Leu Trp Ala Gly Lys Leu
225                 230                 235                 240

Phe His Ile Asp Leu Asn Gly Gln Ser Gly Ile Lys Tyr Asp Gln Asp
```

```
                        245                 250                 255
    Leu Arg Phe Gly Ala Gly Asp Leu Arg Ala Ala Phe Trp Leu Val Asp
                    260                 265                 270

Leu Leu Glu Ser Ala Gly Trp Glu Gly Pro Arg His Phe Asp Phe Lys
                275                 280                 285

Pro Pro Arg Thr Glu Asp Ile Asp Gly Val Trp Ala Ser Ala Ala Gly
            290                 295                 300

Cys Met Arg Asn Tyr Leu Ile Leu Lys Glu Arg Ala Ala Phe Arg
    305                 310                 315                 320

Ala Asp Pro Glu Val Gln Glu Ala Leu Arg Ala Arg Leu Asp Gln
                    325                 330                 335

Leu Ala Glu Pro Thr Ala Ala Asp Gly Leu Gln Ala Leu Leu Ala Asp
                340                 345                 350

Arg Thr Ala Tyr Glu Asp Phe Asp Val Asp Ala Ala Arg Gly Met
            355                 360                 365

Ala Phe Glu Arg Leu Asp Gln Leu Ala Met Asp His Leu Leu Gly Ala
            370                 375                 380

Arg Gly
    385

<210> SEQ ID NO 3
<211> LENGTH: 13
<212> TYPE: PRT
<213> ORGANISM: Streptomyces olivochromogenes

<400> SEQUENCE: 3

Asp Gly Gly Phe Thr Ala Asn Asp Arg Asp Val Arg Arg
 1               5                  10

<210> SEQ ID NO 4
<211> LENGTH: 13
<212> TYPE: PRT
<213> ORGANISM: Streptomyces violaceoniger

<400> SEQUENCE: 4

Asp Gly Gly Phe Thr Ala Asn Asp Arg Asp Val Arg Arg
 1               5                  10

<210> SEQ ID NO 5
<211> LENGTH: 13
<212> TYPE: PRT
<213> ORGANISM: Actinomycetes missouriensis

<400> SEQUENCE: 5

Asp Gly Gly Phe Thr Ser Asn Asp Arg Ser Val Arg Arg
 1               5                  10

<210> SEQ ID NO 6
<211> LENGTH: 13
<212> TYPE: PRT
<213> ORGANISM: Ampulariella sp.

<400> SEQUENCE: 6

Asp Gly Gly Phe Thr Ser Asn Asp Arg Ser Val Arg Arg
 1               5                  10
```

-continued

```
<210> SEQ ID NO 7
<211> LENGTH: 13
<212> TYPE: PRT
<213> ORGANISM: Thermus thermophilus

<400> SEQUENCE: 7

Asp Gly Ala Phe Thr Ser Pro Asp Pro Trp Val Arg Ala
1               5                   10
```

POLYPEPTIDES HAVING GLUCOSE ISOMERASE ACTIVITY AND NUCLEIC ACIDS ENCODING SAME

CROSS-REFERENCE TO RELATED APPLICATIONS

This application claims priority under 35 U.S.C. 119 of Tunisian application no. 99.100 filed on May 26, 1999, the contents of which are fully incorporated herein by reference.

BACKGROUND OF THE INVENTION

1. Field of the Invention

The present invention relates to isolated polypeptides having glucose isomerase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

D-xylose isomerase (D-xylose ketol isomerase, EC 5.3.1.5) catalyzes the conversion of D-xylose to D-xylulose in the first step of xylose metabolism following the pentose phosphate cycle, and of D-glucose into D-fructose as well, hence the enzyme is often referred to as glucose isomerase (GI) [Takasaki et al., 1969, Agric. Biol. Chem. 33: 1527–1534; Jensen V J. and et Rugh, S., 1987, Methods of Enzymol. 136: 256–370]. It is a key enzyme used for the production of sweet high fructose syrups that are used as alternative sweeteners to sucrose or invert sugar in the food and beverage industry.

Most food grade glucose is provided as an enzymatic hydrolysate of corn starch, i.e., corn syrup of commerce. Glucose is generally considered to be 60 to 80% as sweet as sucrose. It has long been known to isomerize glucose to fructose (which is even sweeter than sucrose) employing an enzyme having glucose isomerase activity. This may be a glucose isomerase which has been immobilized upon an inert support such as diethylaminoethyl-cellulose, porous glass or chitin or it can be cells that express glucose isomerase which have been immobilised by cross-linking, e.g. with glutaraldehyde . Detailed descriptions of the enzymatic conversion of glucose to fructose employing glucose isomerase can be found in Hamilton, et al. "Glucose Isomerase a Case Study of Enzyme-Catalysed Process Technology", Immobilized Enzymes in Food and Microbial Processes, Olson et al., Plenum Press, N.Y., (1974), pp. 94–106, 112, 115–137; Antrim, et al., "Glucose Isomerase Production of High-Fructose Syrups", Applied Biochemistry and Bioenqineering, Vol. 2, Academic Press (1979); Chen, et al., "Glucose Isomerase (a Review)", Process Biochem., (1980), pp. 30–35; Chen, et al. "Glucose Isomerase (a Review)", Process Biochem., (1980), pp. 36–41; Nordahl, et al., "Fructose Manufacture from Glucose by Immobiled Glucose Isomerase", Chem. Abstracts, Vol. 82, (1975), Abs. No. 110316h; and Takasaki, "Fructose Production Glucose Isomerase", Chem. Abstracts, Vol. 82, (1975), Abs. No.110316h; and Takasaki, "Fructose Production by Glucose Isomerase", Chem. Abstracts, Vol. 81, (1974), Abs. No. 76474a. In addition, several patents relate to glucose isomerization of which U.S. Pat. Nos. 3,616,221; Re. 28,885 (originally 3,623,953); 3,694,314; 3,708,397; 3,715,276; 3,788,945; 3,826,714; 3,843,442; 3,909,354; 3,960,663; 4,144,127; and, 4,308,349 are representative.

The levels of fructose achievable by the isomerization of glucose with glucose isomerase is limited by the equilibrium of the isomerization reaction. At 65° C., the equilibrium of the reaction has been reported to stand at approximately 51% fructose by weight from a starting substrate of pure dextrose. Under standard conditions, the conversion of glucose to fructose is generally done at 60° C. to 75° C. and at a pH between 7 and 9. In this case, normally only 42% of fructose is obtained because of the equilibrium between glucose and fructose. To shift this equilibrium towards fructose, the temperature must be increased. However, most of the commercial glucose isomerases work at neutral to high pHs and the isomerization at high temperature and pH generates the formation of secondary reactions and undesirable bitter sub-products such D-psicose (Hiromichi, I. Rugh, S. et al. 1995, J. Ferm. Bioeng. 80: 101–103).

To attain syrups of higher fructose content, fractionation systems must be employed which add greatly to the cost of the final product. At higher temperatures, however, the equilibrium becomes more favorable. For example, an enzymatic glucose isomerase process capable of being operated at temperatures of from about 90° C. to 140° C. could be used to directly provide high fructose corn syrups (HFCS) containing 53–60 weight percent fructose on a dry basis, thereby eliminating the need for fractionation and recycle. The tendency of known glucose isomerase systems to undergo thermal denaturation with an accompanying sharp reduction in activity has thus far frustrated attempts to utilize higher temperature regimes to force the equilibrium of the isomerization further in favor of fructose. Moreover, glucose and especially fructose are sensitive reducing sugars which have a marked tendency to form unwanted by-products such as psicose, colored products, color precursors, fructose dianhydrides, mannose, tagatose, and acids when heated to the temperatures necessary to isomerize.

Several thermostable glucose isomerases have been described, e.g. from *Thermus thermophilus* (Dekker K., Sugiura A., et al., 1992, Appl. Microbiol. Biotechnol. 36 727–732); *Thermotoga maritima* (Brown S H. et al., 1993, Biotechn. Bioeng. 41: 878–886); Bacillus sp. (Wuxiang, L. and Jeyaseelan, K., 1993, Biotechn. Lett. 15: 1101–1106) and *Streptomyces rubiginosus* (Wong, H. C. et al., 1991, J. Bacteriol. 173: 6849–6858) and *Chlostridium thermosaccharolyticum* (Menden P G., Opoku , J A., Reizer J, Reizer A et. al, 1994; Gene: 141: 97–101). Nevertheless, the optimal pH of these thermostable glucose isomerases is generally over neutrality.

Thus, presently, there are several glucose isomerases having a high temperature for optimal functionality, such as glucose isomerases studied on the basis of *Streptomyces flavovirens, Streptomyces olivochromogenes, Streptomyces violaceoniger, Lactobacillus brevis*. However, all of these enzymes have a pH optimum which is relatively high (7.5 to 9). Karima Srih-Belghith and Samir Bejar (1998) Biotechnology Letters, Vol 20, No 6, June 1998, pp. 553–556, which is incorporated herein by reference.

It is an object of the present invention to provide improved polypeptides having glucose isomerase activity and nucleic acid encoding the polypeptides.

It is also an object of the present invention to provide a polypeptide having glucose isomerase activity with increased specific activity on glucose, fructose, xylose, and/or xylulose compared to other commercially available glucose isomerases.

SUMMARY OF THE INVENTION

The present invention relates to isolated polypeptides having glucose isomerase activity selected from the group consisting of:

(a) a polypeptide having an amino acid sequence which has at least 95% identity with amino acids of SEQ ID NO:2;

(b) a variant of the polypeptide having an amino acid sequence of SEQ ID NO:2 comprising a substitution, deletion, and/or insertion of one or more amino acids;

(c) a fragment of (a) that has glucose isomerase activity; and (d) a polypeptide having a pH optimum in the range of 5.7 to 6.3 at 60° C., a pH optimum in the range of 6.1 to 6.7 at 90° C. and a temperature optimum of above 90° C.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE DRAWINGS

FIG. 3 shows the schematic representation of the pBKS1 and pBSK2 plasmids. MCS: Muticloning site, MCS1: ApaI, ClaI, SphI, NcoI, KpnI, SstI, EcoRI, HindIII, PstI, BamHI; MCS2: NruI, StuI, XhoI; MCS3: SstI, EcoRI, HindIII, PstI, BamHI, EcoRV; MCS4: NruI StuI, XhoI, BglII, ApaI, NotI, ClaI, SphI, NcoI, KpnI.

FIG. 4 shows the DNA sequence and the deduced amino acid sequence of a Strptomyces sp. SK glucose isomerase (SEQ ID NOS:1 and 2, respectively).

FIG. 5 shows a comparison of the amino acid sequences in the region 100–112 of protein GI SK (XYLA SK) SEQ ID NOS:2 with other glucose isomerases:

Figure 1:
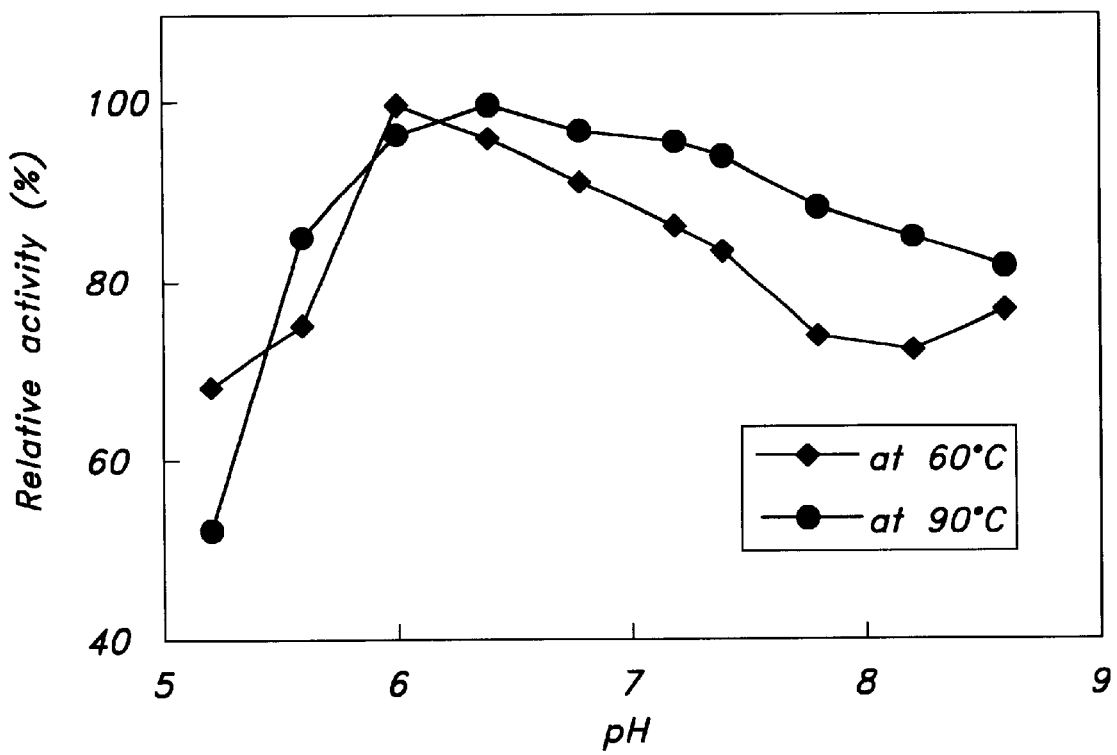
FIG. 1 shows the pH dependence on glucose isomerase activity. The enzyme activity was assayed at 70° C. for 30 min in 0.05 M Tris/maleate buffer, pH 5.2–8.6 as indicated in Materials and methods. One hundred percent activity corresponds to 13 U/mg protein.

XYLA-STROL: Glucose isomerase from *Streptomyces olivochromogenes* SEQ ID NOS:3;

XYLA-STRVO: Glucose isomerase from *Streptomyces violaceoniger* SEQ ID NOS:4;

XYLA-ACTMI: Glucose isomerase from *Actinomycetes missouriensis* SEQ ID NOS:5;

XYLA-AMPSP: Glucose isomerase from Ampulariella sp. SEQ ID NO:6 and

XYLA-THETH: Glucose isomerase from *Thermus thermophilus* SEQ ID NOS:7

DETAILED DESCRIPTION OF THE INVENTION

Polypeptides Having Glucose Isomerase Activity

The term "glucose isomerase activity" is defined herein as a D-xylose isomerase (E.C. 5.3.1.5) activity which catalyzes the conversion of D-xylose to D-xylulose and glucose to fructose. For purposes of the present invention, glucose isomerase activity is determined according to the procedure described by the enzyme assay B in the examples.

The term "syrup" is defined herein as an aqueous solution or slurry comprising carbohydrates such as mono-, oligo- or polysaccharides.

In a first embodiment, the present invention relates to isolated polypeptides having an amino acid sequence which has a degree of identity to amino acids of SEQ ID NO:2 (i.e., the mature polypeptide) of at least about 95%, more preferably at least about 97%, which have glucose isomerase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5).

Preferably, the polypeptides of the present invention comprise the amino acid sequence of SEQ ID NO:2; or a fragment thereof that has glucose isomerase activity. In a more preferred embodiment, the polypeptide of the present invention comprises the amino acid sequence of SEQ ID NO:2. In another preferred embodiment, the polypeptide of the present invention consists of the amino acid sequence of SEQ ID NO:2; or a fragment thereof that has glucose isomerase activity.

A fragment of SEQ ID NO:2 is a polypeptide having one or more amino acids deleted from the amino and/or carboxyl terminus of this amino acid sequence. Preferably, a fragment contains at least 300 amino acid residues, more preferably at least 350 amino acid residues, and most preferably at least 375 amino acid residues.

In a second embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino-or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a third embodiment, the present invention relates to isolated polypeptides having the following physicochemical properties: Temperature optimum of above 90° C. and pH optimum in the range of 5.7 to 6.3 at 60° C. and in the range of 6.1 to 6.7 at 90° C.

In a fourth embodiment, the present invention relates to isolated polypeptides having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N. Y.

The polypeptides of the present invention have at least 20%, preferably at least 40%, more preferably at least 60%, even more preferably at least 80%, even more preferably at least 90%, and most preferably at least 100% of the glucose isomerase activity of the mature polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is expressed intracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a Streptomyces or Streptomyces sp.SK polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well-known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-glucose isomerase polypeptides, e.g., at least about 20% pure, preferably at least about 40% pure, more preferably about 60% pure, even more preferably about 80% pure, even still more preferably about 90% pure, and most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pBSK1 or plasmid pBSK2. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have glucose isomerase activity.

A subsequence of SEQ ID NO:1 is a nucleic acid sequence encompassed by SEQ ID NO:1 except that one or more nucleotides from the 5' and/or 3' end have been deleted.

The present invention also relates to mutant nucleic acid sequences comprising at least one mutation in the mature polypeptide coding sequence of SEQ ID NO:1, in which the mutant nucleic acid sequence encodes a polypeptide which consists of amino acids of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Streptomyces sp. SK, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20].

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et aL, 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for glucose isomerase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Methods for Producing Mutant Nucleic Acid Sequences

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids of SEQ ID NO:2 or a fragment thereof which has glucose isomerase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, ribosome binding site, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, trnmcated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Streptomyces erythraeus* gene (ermE), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et aL, 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fingal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol, thiostrepton, apramycin or tetracycline resistance. Suitable markers for yeast host cells are ADE2, HIS3, LEU2, LYS2, MET3, TRP1, and URA3. Selectable markers for use in a filamentous fingal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, pUB110, pE194, pTA1060, and pAMβ13 permitting replication in Bacillus and pIJ101 permitting replication in Streptomyces. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothernophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971,*Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fingal cell.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous flngi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillusfoetidus, Aspergillusjaponicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fingal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Streptomyces, and more preferably Streptomyces sp. SK.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1, wherein the mutant nucleic acid sequence encodes a polypeptide which consists of amino acids of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having glucose isomerase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Vicia faba promoter from the legumin B4 and the unknown seed protein gene from Viciafaba (Conrad et al., 1998, *Journal of Plant Physiology* 152: 708–711), a promoter from a seed oil body protein (Chen et al., 1998, *Plant and Cell Physiology* 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *BiolTechnology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, Plant Journal 2: 275–281; Shimamoto, 1994, *Current Opinion Biotechnology* 5: 158–162; Vasil et al., 1992, *BiolTechnology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having glucose isomerase activity of the present invention under conditions conducive for production of the polypeptide; and (b) recovering the polypeptide.

Compositions

In a still further aspect, the present invention relates to compositions comprising a polypeptide of the present invention. Preferably, the compositions are enriched in a polypeptide of the present invention. In the present context, the term "enriched" indicates that the glucose isomerase activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus*, *Aspergillus awamori*, *Aspergillus niger*, or *Aspergillus oryzae*, or Trichoderma, Humicola, preferably *Humicola insolens*, or Fusarium, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having glucose isomerase activity.

Preferably the glucose isomerase may be used within the food industry, particularly in the starch industry for production of high fructose corn syrups, which then can be used in the food and beverage industries for production of cakes, baked product, soft drinks etc.

The present invention is further described by the following examples which should not be construed as limiting the scope of the invention.

EXAMPLES

Introduction

The invention is characterised by the following stages:

a) The isolation of a strain of Streptomyces from a sample of Tunisian soil, said Streptomyces comprises a glucose isomerase;

b) The determination of the physical-chemical properties of the enzyme;

c) The utilisation of the strain and the enzyme for the bioconversion of a solution of pure glucose to a solution of isoglucose (a mixture of glucose and fructose) or for the bioconversion of a glucose syrup to a fructose syrup.

d) The cloning of the gene coding for said enzyme in a model strain of *E. coli* e) The determination of the nucleotide sequence of said gene as well as determination of the amino acid sequence of the enzyme.

f) Analysing the amino acid sequence and elucidate the originality of said amino acid sequence.

The GI of the present invention has been discovered in an isolated strain of thermophilic Streptomyces (thermophile Streptomyces sp. SK), which was isolated from a sample of Tunisian earth. GI SK possesses very interesting characteristics, in particular with respect to the tolerance for low pH since the optimum pH is found to be 6,4 at 90° C. This property in addition to the thermoactivity makes it possible to perform an isomerisation reaction at low pH and high temperature, which is very desirable from an industrial point of view. Furthermore, the cloning of the gene coding for this enzyme, as well as the nucleotide sequence and amino acid sequence of the enzyme is disclosed. The amino acid sequence is characterised by certain originalities which may explain the interesting properties of the enzyme compared to other glucose isomerases. With regard to the amino acid sequence, the 3 most evident originalities are found in the region 100–110 amino acid residues of the protein.

Materials and methods

Growth conditions

For the production of glucose isomerase, Streptomyces sp. SK strain was grown in a production medium containing 3% (w/v) peptone, 0.5% yeast extract, 1% xylose, 0.1% $MgSO_4$, 7 $H_2O$ and 0.01% (w/v) $CoCl_2$ at 30° C. for 48 hours on an orbital shaker rotating a 250 rpm.

Bacterial strains

*Escherichia coli* TG1 (supE hsdΔ5 thi Δ(lac-proAB) F1 traD36proAB$^+$ lacIq lacZΔM15 and HB101 (F hsdS2 recA13 ara$^-$14 pro A2 lacY1 galk2 rps L20xyl$^-$5 mtl sup E44) were used as host strains. PBSK1 and pBSK2 (this work). PUT57, a derivative of pUC19. PUT670, a plasmid carrying the xylA gene of *S. Olivochromogenes*, has already been described (Bejar S. et al., 1994, Biotechnol. Lett. 16: 1259–1264).

Enzme assays

A) The mycelium pellets were collected by centrifugation and resuspended on a 0.05 M phosphate buffer pH 7 containing 0.1 mM phenylmethanesulfonyl fluoride. The cell-free enzyme fraction was obtained by the disruption of the cells for 5 min with a type B-12 sonicator (Branson Ultrasonics) at 0C. This step was followed by centrifugation at 30000 g. for 30 min. The supernatant was taken as a crude extract. Protein content was determined by the method of Bradford, MM (1976) Anal. Biochem.72:248–254. The enzyme activity was assayed in a reaction mixture containing 0.9 M glucose, 10 mM $MgSO_4$, 1 mM $CoCl_2$, 50 mM Tris/maleate buffer pH 5.2–8.6 (as indicated) and the enzyme (50 μl of an appropriate diluted crude extract) in a total volume of 1 ml. After incubation at different temperatures for 30 min, 0.5 ml was poured into 4.5 ml 0.5 M perchloric acid to stop the reaction. The fructose formed was determined by the cysteine carbozole sulfuric acid method (Dische Z. and Borenfreund, E. 1951, J. Biol. Chem 192: 583–587). One Unit of isomerase activity was defined as the amount of enzyme needed to produce 1 lmol of product per min under the assay conditions.

B) The enzyme activity on fructose substrate was assayed by mixing 100 microliter enzyme solution with 100 microliter activator solution (40 mM MOPS, pH 7.5, 1M $Mg^{2+}$, 1.73 M NaCl and 4 mM $Co^{2+}$) for 5–60 min, adding 200 microliter substrate solution (15% (W/V) fructose (Sigma F-2543), 20 mM MOPS, pH 7.5), incubating for 30 min at 60° C., adding 600 microliter stop solution (0,5 M perchloric acid), and detecting glucose formed by mixing 20 microliter stopped reaction mixture with 200 microliter GOD-PERID solution (Boehringer Mannheim) for 40 min. and measuring optical density at 650 nm. One unitF of glucose isomerase activity on fructose substrate is defined as the amount of enzyme needed to produce 1 micromole of product per min under these assay conditions.

Manipulation of DNA

Digestion of DNA with restriction endonucleases, separation of fragments by agarose gel electrophoresis, dephosphorylation with alcaline calf intestinal phosphatase, ligation of DNA fragments and transformation with plasmid DNA were performed as described by Sambrook et al. (1989) for *E. Coli*, and by Hopwood DA et aL (1985) (A Laboratory Manual, John Innes Foundation, Norwich England) for Streptomyces or as recommended by the enzyme manufacturers. Screening clones by radiolabelled probe was performed as previously described by Grunstein M. and Wallis J. (1979), Mehods of Enzymol. 136:256–370.

Example 1

Stage (a) consisted in isolation of the strain Streptomyces sp. SK from a sample of soil taken from a Tunisian hot spring. We have isolated several strains of thermophile actinomycetes on selection medium containing xylose as the sole carbon source. All strains that grow in this type of medium are considered to have a glucose isomerase activity. Preliminary studies of the glucose isomerase activities of these isolated strains indicated that a strain which has been identified as a strain of Streptomyces (Streptomyces sp. SK) has interesting properties, reference is made to the study described in Karima Srih-Belghith and Samir Bejar (1998) Biotechnology Letters, Vol 20, No 6, June 1998 pp 553–556, which is incorporated herein by reference. In this study, which is part of the present invention, soil samples collected from different regions of Tunesia were spread directly on different solid media containing 25 μg of novobiocin per ml to inhibit fungal growth. After incubation at 45° C. for 24 h, colonies were picked and propagated on a gruel medium This strain (Streptomyces sp. SK) was sporulated at 45° C. for 2 to 3 days in a gruel solid medium containing 3% (w/v) gruel, 0.5% yeast extract, 0.5% glucose and 2% agar (pH 6.8). Gruel is a sub-product of wheat grinding which contains approximately 12% (w/v) protein, 55% (w/v) starch and 33% (w/v) other oligosaccarides. We have noted that generally Streptomyces strains sporulated more quickly in this medium as compared to other known media.

All of the isolated thermophilic Streptomyces have a xylose isomerase activity since they grew on a minimal medium containing xylose as a unique source of carbon. Furthermore, the xylose isomerase activity of these strains was investigated at pH 6 and 70° C. Preliminary studies allowed us to focus our attention on one strain, Streptomyces sp. SK, which has the highest glucose isomerase activity under the conditions used, and is able to grow up to 55° C. on solid media.

Example 2

The next stage (b) consisted in determination the physical-chemical characteristics of the enzyme, in particular pH and temperature optimum. The enzyme activity was tested at different pH and temperature as described in "Material and methods". The glucose isomerase of the present invention is expressed intracellularly in the bacteria cells . The cells can be separated by filtration or by centrifugation from the culture media and used directly as a source for glucose isomerase. The cells may also be separated by filtration followed by disruption of the cells by methods known in the art. The hereby produced disrupted cells and the liberated content can be used as a source of glucose isomerase.

Figure 2:
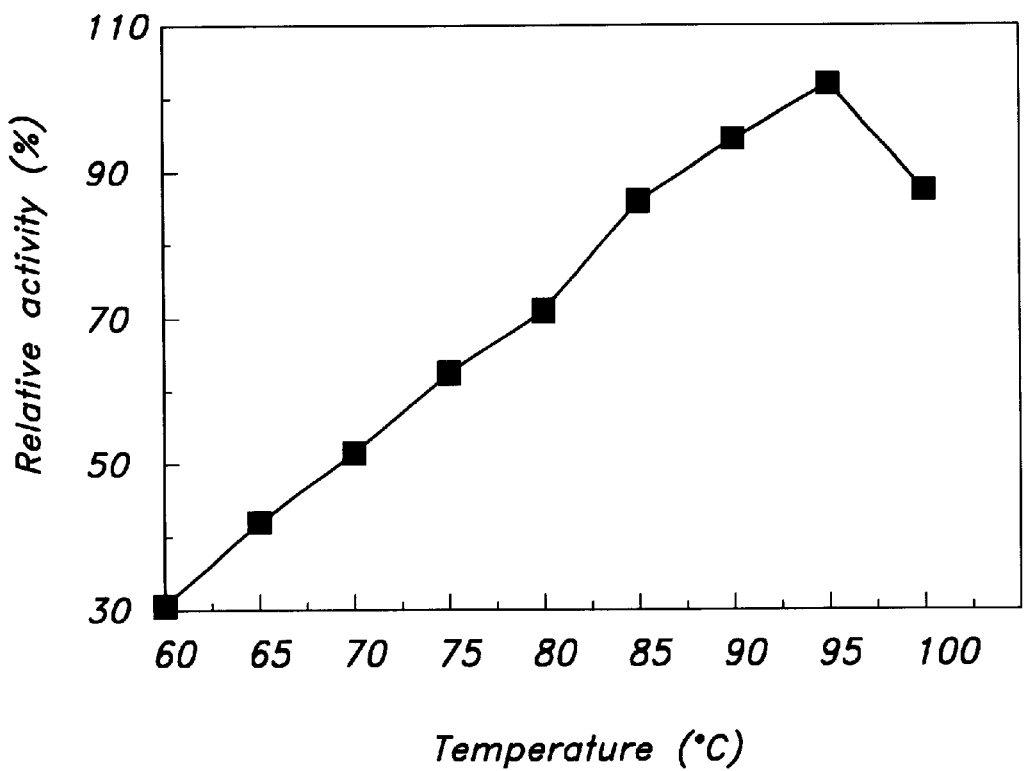
FIG. 2 shows the temperature dependence on glucose isomerase activity investigated at pH 6 (in 0.05 M Tris maleate buffer). Activity assay, 30 min. One hundred percent activity corresponds to 13 U/mg protein.

FIG. 1 shows the effect of pH on the glucose isomerase enzyme derived from the strain Streptomyces sp. SK. This study shows that GI SK with respect to its activity tolerates a wide pH range and has a pH optimum of 6 at 60° C. and 6.4 at 90° C. This activity has a broad pH range of 5.5–8.0 with an optimum of 6 at 60° C. and 6.4 at 90° C. This is the first GI described from Streptomyces that tolerates a low pH. Liu et al. (1996) reported a glucose isomerase from Thermoanarerobacterium with an acid pH optimum (6.4 at 60° C. and 6.8 at 80° C.). However, the latter has an optimal temperature (Tapr) of 80° C., while Streptomyces sp. SK (FIG. 2) has an optimum temperature of above 90° C.

This interesting property constitute a very important aspect of GI SK. In fact, this property makes it possible to perform the isomeration step at a relatively low pH value which reduces the formation of secondary reactions generating products with a bitter taste. Furthermore, GI SK possesses a high temperature optimum. In fact, the study on the effect of the temperature on GI SK shows (FIG. 2) that the enzyme is thermoactive since the optimum temperature is above 90° C. The most thermostable and themoactive glucose isomerases are those of *Thermotoga thermophilus* (Dekker et al., 1992) and *Thermotoga maritima* (Brown et al., 1993), with respective $T_{opt}$ of 95 and 105° C. However, these enzymes are less outstanding than the glucose isomerase of Streptomyces sp. SK regarding the activity at a lower pH since the pH optimum at 80° C., is 7 for *To thermophilus* and 7.5 for *T. maritima*. To test its stability with respect to temperature, the Streptomyces sp. SK glucose isomerase was incubated at 80 and 90° C. at pH 6. This study shows that the enzyme was stable at 80° C. for more than 5.5 hours, while at 90° C. its activity declined with a half-life of approximately 5 hours.

Example 3

The next stage (c) consisted in demonstrating the capacity of the enzyme in bioconversion of a solution of glucose to a mixture of glucose and fructose. For this, in Example 3, was used a crude extract containing glucose isomerase activity. It is evident that it is possible and realisable to use enzymes in a semi purified form or enzyme purified in either a free soluble or in an immobilised form, or even intact cells in suspension or in immobilised form.

Example 3A: Bioconversion of a solution of pure glucose to a mixture of glucose and fructose.

The strain Streptomyces sp. SK possesses a glucose isomerase which is effective and capable of finctioning at a high temperature and at a relatively low pH. This strain was cultivated under well defined conditions. The cells (mycelium) where recuperated by centrifugation and disrupted by a well-known method. The GI SK activity is in the supernatant after ultrafiltration. This crude enzyme preparation was used for bioconversion.

The conditions used for the bioconversion are the following: To a 5 ml solution of 0.8 M glucose, 10 mM $MgSO_4$, 1 mM $CoCl_2$, 50 mM Tris/maleate pH 6.4 was added 200 µl of the enzyme preparation. The temperature is maintained at 85° C. for 120 min to effectuate the bioconversion. Subsequently, the amount of fructose formed is determined chromatographically by HPLC.

This chromatogram shows that the enzyme preparation is capable of bioconverting a part of the glucose to fructose. This bioconversion can presumable reach a maximum of about 55% if the reaction time is prolonged and/or by addition of a larger amount of enzyme.

Example 3B: Conditions for bioconversion of a DE>95 glucose syrup originating from a hydrolysate of coarsely grounded flour and comparison with GI of type Q from Novo Nordisk A/S.

In this example there is provided for information the conditions for bioconversion of a DE>95 glucose syrup obtained from an amylolytical hydrolysate of coarsely grounded flour by GI SK or by glucose isomerase type Q from Novo Nordisk A/S are provided.

The composition of a DE/95 glucose syrup is approximately as follows:

| DE (Dextrose equivalents) | 95–98% |
| Glucose | 94–96% |
| Maltose | 2–7% |
| Other maltodextrins | 0–2% |

In this example we have used intact cells comprising GI SK activity. The strain is cultivated under well defined conditions. Subsequently, the cells are collected by centrifugation. These cells are used without any further treatment for the batchwise isomerization. However, it should be noted that other types of enzyme preparations in the form of immobilised cell or soluble enzymes (which is the case for Example 1) or immobilised enzymes can be used as well, under appropriate conditions.

The conditions for bioconversion by the cells of the strain Streptomyces sp. SK or by the type Q enzyme are as follows:

To 15 ml of a solution of 0.8 M glucose (syrup DE>95), 10 mM $MgSO_4$, 1 mM $CoCl_2$, 50 mM Tris/maleate pH 6.4 is added either:

a) 0.1–0.2 g of the enzyme preparation named "Sweetzyme type Q" commercialised by Novo Nordisk A/S. This is a preparation of immobilised intact cells of B. coagulans which is recommended for batchwise bioconversion;

b) 0.2–0,3 g mycelium (13–15% dry weight) of the strain Streptomyces sp. SK containing GI SK.

The same amount of enzyme unit has been used for each of these two experiments and the temperature is kept at 85° C. for 120 min under slow agitation to carry out the bioconversion. Subsequently, the insoluble glucose isomerase, is isolated from the solution by centrifugation, and the amount of fructose produced is determined chromatographically by HPLC.

This chromatogram clearly shows that the cells of Streptomyces sp. SK containing GI SK are capable of bioconverting glucose syrup DE>95 (in this case produced as a hydrolysate of coarsely grounded flour) to an isoglucose syrup, a mixture of glucose and fructose. Even better, this example shows that at the employed pH (6.4) which is desired in order to obtain a better exploitation on an industrial scale, the yield obtained by bioconversion with GI SK is greater than that obtained with GI Q and this is evidently for the same amount of enzyme (based on units) used for the reaction. This clearly confirms the tolerance of GI SK for a low pH value.

Example 4

The next stage (d) consists of cloning of the gene coding for glucose isomerase from Streptomyces sp. SK. It is well-known that cloning of a gene is a very important stage, which render possible a better characterisation of the enzyme in question and construction of strains which express the corresponding activity. For the cloning we have produced a gene bank of the strain Streptomyces SK in a reference strain of E. coli by use of a vector having a high copy number. After the screening of the gene bank with a specific probe we have localised a clone carrying the plasmid pBSK1 (FIG. 3) comprising the gene xylA coding for GI SK. The E. coli strain that carry the plasmid pBSK1 also expresses GI SK activity in the interior of the cell. This renders possible an exploitation of these recombinant or derived strains for the production of GI SK. Upon determination of the gene encoding the GI from Streptomyces sp. SK, the DNA sequence was deposited in EMBL as acc. no Y15518 on 1 Feb. 1, 1999.

Molecular cloning of the xylA SK gene

Chromosomal DNA of Streptomyces sp. SK strain was partially digested by Sau3A endonuclease; and DNA fragments with approximately 4–10 kb of size were inserted into dephosphorylated BglII linearised pUT57 vector. After transformation of E. Coli TG1 strain, the recombinant clones were transferred to nitrocellulose filters. These clones were screened by using an α32 (P) radio-labelled probe which consisted of a 500 pb DNA fragment from the 5' end from xylA from S. Olivochromogenes, obtained from pUT670 plasmid (Bejar et al., 1994).

Among 3000 recombinant clones screened, three clones showing a distinct hybridization signal were obtained. One clone, having a plasmid pBSK1, with the largest insert (6.2 kb) was retained. Furthermore, we have demonstrated that HB 101/pBSK1 strain gives a red color in MacConkey agar plates supplemented with 1% (w/v) xylose. This proves that the pBSK1 plasmid complemented the E. Coli xyl-5 mutant strain HB101. Further experiments (not shown) using two probes of 500 bp carrying the 5' or the 3' end of xylA from S. Olivochromogenes allowed us to delimit and orient the xylA SK gene on the plasmid pBSK1 (FIG. 3). The NruI—NruI fragment carrying the entire xylA SK gene was subcloned into SmaI linearised pUT57 to give pBSK2 plasmid (FIG. 3).

Example 5

After the cloning of the gene xylA SK, the next stage (e) consisted in determination the nucleotide sequence for the gene thereby deducing the amino acid sequence from said nucleotide sequence. In order to accomplished this, the pBSK1 insert carrying the gene xylA SK was subcloned into a suitable vector. Subsequently, the nucleotide sequence of 1546 base pair comprising the gene xylA SK was determined (FIG. 4) by use of methods for nucleotide determination traditionally used by the person skilled in the art.

Analyses of this nucleotide sequence has subsequently permitted the finding of an open reading frame which has been identified as being the sequence for the gene xylA coding for GI SK. This reading frame codes for at protein with a theoretical molecular weight of 42.7 kDa.

Example 6

Analyses (Stage f) of the corresponding amino acid sequence of the protein XYLASK have revealed a high homology with other glucose isomerases (Table 1), but it has at the same time also shown the following originalities:

1) A higher content of hydrophobic amino acid residues than other xylose isomerases, in particular in comparison with xylose isomerases from other Streptomyces (Table 1)
2) The following specific substitutions S62A, S69A, S332A, and E348A, and 3 more situated in the region 100–110 (FIG. 5) of the protein D100→A100, G102→A102 and D109→A109.

These changes, as well as the high hydrophobicity content, permits a higher flexibility of the enzyme, which explains the capacity of the enzyme to function at low pH and high temperature. Accordingly, the special physical-chemical properties are linked to a peculiar amino acid sequence.

TABLE 1

Comparison of GI SK with other glucose isomerases

| Strains | % Identity | % of hydrophobic amino acid residues |
|---|---|---|
| Streptomyces sp SK | 100 | 47.4 |
| S. olivochromogenes | 94.04 | 45.0 |
| S. violaceoniger | 92.49 | 46.1 |
| S. albus | 91.97 | 45.0 |
| Thermus thermophilus | 58.81 | 46.1 |
| B. Subtilis | 13.21 | 46.6 |
| E. coli | 10.62 | 46.9 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence selected from the group consisting of:
   (a) a nucleic acid sequence comprising the sequence of SEQ ID NO:1 and
   (b) a nucleic acid sequence encoding a polypeptide having the amino acid sequence of SEQ ID NO:2.

2. A nucleic acid construct comprising the nucleic acid sequence of claim 1 operably linked to one or more control sequences that direct the production of the polypeptide in a suitable expression host.

3. A recombinant expression vector comprising the nucleic acid construct of claim 2.

4. A recombinant host cell comprising the nucleic acid construct of claim 2.

5. A method for producing a glucose isomerase polypeptide, said method comprising: (a) cultivating a host cell of claim 4 under conditions suitable for production of the polypeptide; and (b) recovering the polypeptide from the host cell or supernatant, or recovering the host cell containing the polypeptide.

* * * * *